US010668086B2

(12) United States Patent
Kuusisto et al.

(10) Patent No.: US 10,668,086 B2
(45) Date of Patent: Jun. 2, 2020

(54) CHOLESTEROL LOWERING CAPSULES

(71) Applicant: RAISIO NUTRITION LTD, Raisio (FI)

(72) Inventors: Päivi Kuusisto, Raisio (FI); Ingmar Wester, Raisio (FI); Leena Koponen, Raisio (FI); Jari Ekblom, Raisio (FI); Jouni Niemela, Raisio (FI)

(73) Assignee: RAISIO NUTRITION LTD, Raisio (FI)

( * ) Notice: Subject to any disclaimer, the term of this patent is extended or adjusted under 35 U.S.C. 154(b) by 0 days.

(21) Appl. No.: 15/518,956

(22) PCT Filed: Oct. 17, 2014

(86) PCT No.: PCT/EP2014/002817
§ 371 (c)(1),
(2) Date: Apr. 13, 2017

(87) PCT Pub. No.: WO2016/058623
PCT Pub. Date: Apr. 21, 2016

(65) Prior Publication Data
US 2017/0224707 A1   Aug. 10, 2017

(51) Int. Cl.
| A61K 9/00 | (2006.01) |
| A61K 9/48 | (2006.01) |
| A23L 33/00 | (2016.01) |
| A23L 33/11 | (2016.01) |
| A61K 47/24 | (2006.01) |
| A61K 9/127 | (2006.01) |
| A61K 31/575 | (2006.01) |

(52) U.S. Cl.
CPC ............ *A61K 31/575* (2013.01); *A23L 33/11* (2016.08); *A23L 33/40* (2016.08); *A61K 9/00* (2013.01); *A61K 9/127* (2013.01); *A61K 9/4833* (2013.01); *A61K 9/4858* (2013.01); *A61K 9/4875* (2013.01); *A61K 47/24* (2013.01); *A23V 2002/00* (2013.01)

(58) Field of Classification Search
CPC .. A61K 31/575; A61K 9/4833; A61K 9/4875; A61K 9/4858; A61K 9/00; A61K 9/127; A61K 47/24; A61K 47/44; A23L 33/40; A23L 33/11; A23V 2002/00
See application file for complete search history.

(56) References Cited

U.S. PATENT DOCUMENTS

| 6,174,560 | B1 | 1/2001 | Miettenen et al. |
| 2003/0203854 | A1* | 10/2003 | Pischel ............... A23D 7/0053 514/23 |
| 2003/0212046 | A1 | 11/2003 | Spilburg |
| 2005/0153948 | A1 | 7/2005 | Spilburg |
| 2006/0093661 | A1 | 5/2006 | Spilburg |
| 2008/0124387 | A1 | 5/2008 | Spilburg |
| 2008/0187645 | A1* | 8/2008 | Ekblom ............... A23D 7/0056 426/602 |
| 2009/0088393 | A1 | 4/2009 | Spilburg |
| 2010/0113368 | A1* | 5/2010 | Edens ................. A23L 2/52 514/1.1 |
| 2011/0111009 | A1 | 5/2011 | Spilburg |
| 2015/0030671 | A1 | 1/2015 | Spilburg |

FOREIGN PATENT DOCUMENTS

EP   1925294 A1   5/2008

OTHER PUBLICATIONS

International Search Report and Written Opinion of the ISA for PCT/EP2014/002817, ISA/EP, Rijswijk, NL, dated Feb. 18, 2015.
• Ottestad et al. (Atherosclerosis Jun. 2013; 228(2):421-5).
• Lubinus et al. (Eur. J. Nutr. 2013, 52(3):997-1013)
• Esche et al. (J. Agric. Food Chem. 2012, 30;60(21):5330-9.

\* cited by examiner

*Primary Examiner* — Snigdha Maewall
(74) *Attorney, Agent, or Firm* — Harness, Dickey & Pierce, P.L.C.

(57) ABSTRACT

The invention relates to a capsule consisting of a shell and a filling, which contains plant sterol ester and/or plant stanol ester and emulsifier. The capsule is suitable for lowering serum LDL cholesterol level.

29 Claims, No Drawings

CHOLESTEROL LOWERING CAPSULES

CROSS-REFERENCE TO RELATED APPLICATIONS

This application is a 371 U.S. National Stage of International Application No. PCT/EP2014/002817, filed Oct. 17, 2014. The disclosures of the above application are incorporated herein by reference.

FIELD OF THE INVENTION

The present invention relates to the field of nutrition and health, and especially to capsules for lowering serum LDL cholesterol level.

BACKGROUND OF THE INVENTION

Cardiovascular disease is counted among the most common diseases in Western countries and its occurrence is increasing also in Asian countries. The most important individual risk factor is elevated serum LDL cholesterol level, and therefore, lowering of the serum concentrations of LDL cholesterol is the most effective single measure regarding both prevention and effective treatment of cardiovascular disease.

The most important drugs for reduction of serum cholesterol levels are the statins, which function primarily by inhibiting the synthesis of cholesterol, mainly in the liver. The most common side effects of the statins are gastrointestinal. Other less common side effects include headache, dizziness, rash, and sleep disturbances. In addition, statins may cause both liver damage and muscle disorders, and they have been reported to increase the risk of type II diabetes.

As an alternative to cholesterol lowering drugs, or in addition to them, also life style changes can reduce the risk of cardiovascular diseases. In particular increasing physical exercise and/or adopting healthy diets recommended by governments or non-governmental associations are beneficial. An additional nutritional way to reduce serum LDL cholesterol levels is the use of cholesterol lowering functional foods that can be consumed as part of any conventional diet. This alternative has been greatly welcomed by consumers.

Food products enriched with components having a cholesterol lowering effect have been commercially available for almost 20 years. Such functional food products usually contain plant sterols and/or plant stanols and especially their fatty acid esters as active ingredients. Plant sterols have since the early 1950's been known to reduce serum cholesterol levels. U.S. Pat. No. 6,174,560 describes plant stanol fatty acid esters, a method for their preparation, and the cholesterol lowering effects thereof. An intake of 2 g per day of plant stanols is reported to lower serum LDL cholesterol levels in man up to 14%. Benecol is a well-known trademark for plant stanol ester containing products and nowadays plant stanol ester is used in a variety of food products. Many of these products, e.g. margarine-type spreads and drinkable and spoonable yoghurts, need continuous refrigeration. However, many consumers would prefer to have their daily dose of plant sterols and/or plant stanols available in a product that can be carried along wherever they go, e.g. as a dietary supplement.

One of the most common type of dietary supplements are capsules, such as soft gelatin capsules, so called softgel capsules. Capsules consist of a shell and a filling containing the active ingredient.

Softgel capsules containing plant sterol ester and/or plant stanol ester have already been disclosed. The clinical trials conducted with these softgel capsules have yielded variable results. Most clinical studies with plant sterol ester and/or plant stanol ester softgel capsules have failed to deliver the expected serum LDL cholesterol lowering efficacy compared with the corresponding clinical trials with plant sterol ester and/or plant stanol ester functional food products. In a recent study of Ottestad et al. (Atherosclerosis 2013 June; 228(2):421-5) a softgel capsule containing plant sterol ester (2 g/d plant sterols) did not lower serum LDL cholesterol in hypercholesterolemic subjects. The authors concluded that this delivery system (softgel capsules) of plant sterol ester does not seem to give the expected LDL cholesterol reduction and thus the clinical relevance of the consumption of plant sterol ester capsules remains uncertain.

The softgel capsules that have been commercially available or are currently on the market contain plant sterol ester and/or plant stanol ester as such or mixed with vegetable oil, e.g. 80% plant sterol ester and/or plant stanol ester and 20% vegetable oil. Usually the recommended daily amount of plant sterols and/or plant stanols is 2 g, which means that the daily minimum required amount of plant sterol ester and/or plant stanol ester is about 3.4 g. Therefore the size of capsules is big, delivering about 1 g plant sterol ester and/or plant stanol ester in each soft gelatin capsule. For optimal cholesterol lowering efficacy plant sterol ester and/or plant stanol ester capsules are recommended to be consumed with a meal.

Because the clinical relevance of plant sterol ester and/or plant stanol ester capsules has been questioned, there remains a need for improved plant sterol ester and/or plant stanol ester capsules that will deliver the expected serum LDL cholesterol lowering effect when consumed as recommended.

BRIEF DESCRIPTION OF THE INVENTION

The present invention is directed to a capsule comprising a shell and a filling, in which the filling comprises plant sterol ester and/or plant stanol ester in an amount of at least 85% by weight and emulsifier in an amount of at least 1.0% by weight.

The present invention is further directed to a method for preparing the capsule.

The present invention is still further directed to the capsule for use as a medicament and/or for lowering serum LDL cholesterol level.

DETAILED DESCRIPTION OF THE INVENTION

It is thus an object of the present invention to provide a capsule comprising a shell and a filling that contains plant sterol ester and/or plant stanol ester in an amount of at least 85% by weight and emulsifier in an amount of at least 1.0% by weight of the filling.

It has now been found that the disintegration of some prior known capsule fillings containing plant sterol ester and/or plant stanol ester in a simulated gastric fluid test at 38° C. is not optimal, but very slow and inefficient. Presumably the slow and inefficient disintegration has hampered the cholesterol lowering efficacy of these capsules.

Thus the present invention provides a capsule comprising a shell and a filling containing a high amount of plant sterol ester and/or plant stanol ester, in which capsule the filling is rapidly disintegrated in the stomach or in conditions resembling the gastric conditions. It has now surprisingly been found that a capsule filling containing plant sterol ester and/or plant stanol ester and emulsifier in certain amounts is rapidly disintegrated in a simulated gastric fluid test. It is now hypothesized that the rapid disintegration of the capsule filling of the invention contributes to a good serum LDL cholesterol lowering efficacy of capsules containing this filling.

An advantage of the capsule filling of the present invention is that it contains a high concentration of plant sterol ester and/or plant stanol ester. Thus the consumer needs to take only a few capsules per day to obtain the daily effective dose of plant sterol ester and/or plant stanol ester. All the ingredients used in the capsule filling of the present invention are food grade. Preferably ingredients that can be used with quantum satis principle are used. This means that the ingredients can be used in accordance with good manufacturing practice and no limitation will be imposed on the consumption of the capsule product.

Thus, the present invention is preferably directed to a capsule consisting of a shell and a filling comprising plant sterol ester and/or plant stanol ester in an amount of at least 85% by weight and emulsifier in an amount of at least 1.0% by weight of the filling.

By "capsule" is in this disclosure meant dosage forms which consist of hard or soft shells of various shapes and filling volumes, and a filling containing the active ingredient. Capsules are intended for oral administration. Hard capsules have shells consisting of two cylindrical sections, one end of which is rounded and closed, the other open. The filling is put into one of the sections which is then closed by slipping the other section over it. If the filling is liquid or semi-solid, the capsule halves are sealed together. The hard shell is usually made of gelatin and water together with coloring and opacifying agent. The present invention is especially directed to soft capsules, which are also called "softgel capsules". By "softgel capsules" is meant one-piece, hermetically sealed capsules. The softgel capsule shell is usually based on gelatin, water and plasticiser(s), and optionally also coloring and opacifying agent. For example glycerol and/or sorbitol or its derivatives can be used as a plasticiser. There are also polysaccharide-based softgel capsule shells that contain e.g. starch and/or carrageenan. The softgel capsules can be manufactured by the so called rotary-die encapsulation process. In this process, the encapsulation of the filling is made simultaneously with the formation of the capsule shell. First two plasticized films called ribbons are formed from the shell mass. Each ribbon is passed over a die and sealed to the other ribbon at the point where the two dies meet while filled simultaneously. Then the filled capsules are dried.

By "filling", i.e. "capsule filling", is meant the fill composition inside the capsule shell. In this disclosure, the filling contains the active ingredient, i.e. plant sterol ester and/or plant stanol ester. The filling preferably has a solid fat content (SFC) of at least 20%, more preferably at least 25%, still more preferably at least 30%, and most preferably at least 35% at 20° C. The solid fat content can be measured e.g. by conventional NMR technique by using a serial tempering method starting at 10° C.

By "disintegration" is in this disclosure meant disintegration of the capsule filling in a simulated gastric fluid test. In the test a simulated gastric fluid is used as the liquid medium. It has low pH (e.g. 1-2). The speed of disintegration of the capsule filling can be monitored as e.g. described in the examples of this disclosure. The capsule filling is first produced and let to crystallize at room temperature for at least 70 hours in moulds as described in the Examples of this disclosure. The capsule filling is then placed in the simulated gastric fluid at 38° C. with mixing (e.g. 150-160 oscillations per minute), and its disintegration is visually observed. The time when the capsule filling is disintegrated (i.e. it is broken into several disintegrated particles and/or forms a cloudy liquid) is used as a measure of the speed of disintegration. As used here, the definition of disintegration does not take into account the disintegration of the capsule shell, but only the capsule filling. However, for optimal cholesterol lowering effect also the capsule shell shall disintegrate as fast as possible. Determination of disintegration times of the capsule shell can be carried out according to US Pharmacopeia USP29-NF24. The shell is preferably disintegrated within 15 minutes. Such shells are known to a skilled person in the art.

When used here in connection with the disintegration test, by "disintegrated particle" is meant visually distinguishable pieces and/or droplets of the filling that have disintegrated from the filling in the simulated gastric fluid test. The disintegrated particle can be in solid, semi-solid or liquid form.

The capsule filling of the present invention disintegrates rapidly in the stomach in order to provide an effective serum cholesterol lowering in humans. Preferably several disintegrated particles and/or a cloudy liquid is formed of the capsule filling in the simulated gastric fluid test within 20 minutes, more preferably within 15 minutes, and most preferably within 10 minutes.

The capsule filling of the present invention contains at least 85%, preferably at least 87%, more preferably at least 90% and most preferably at least 92% by weight plant sterol ester and/or plant stanol ester. The capsule filling contains at most 99%, preferably at most 98% and most preferably at most 97% by weight plant sterol ester and/or plant stanol ester.

As used here, the term "plant sterol ester and/or plant stanol ester" refers to plant sterols and/or plant stanols in esterified form. The term "plant sterol" includes 4-desmethyl sterols and 4-monomethyl sterols and the term "plant stanol" includes 4-desmethyl stanols and 4-monomethyl stanols. Typical 4-desmethyl sterols are sitosterol, campesterol, stigmasterol, brassicasterol, 22-dehydro-brassicasterol and δ5-avenasterol. Typical plant stanols are sitostanol, campestanol and their C24-epimers. The term "plant sterols and/or plant stanols" includes all possible mixtures of named sterols and/or stanols as well as any individual sterol and/or stanol.

In this invention plant sterols and/or plant stanols are esterified with a carboxylic acid or with a blend of carboxylic acids and are called "plant sterol ester and/or plant stanol ester". Examples of suitable carboxylic acids are fatty acids. The fatty acids are aliphatic, have 4-24 carbon atoms, and are saturated, monounsaturated or polyunsaturated. The physical properties of the plant sterol ester and/or plant stanol ester can be modified by changing the fatty acid moiety of the molecule. Preferably the plant sterols and/or plant stanols are esterified with vegetable oil based fatty acids. Preferred are fatty acids of rapeseed oil, soybean oil, sunflower oil and corn oil. Preferably plant sterol ester and/or plant stanol ester has a solid fat content (SFC) of at least 20%, more preferably at least 25%, still more preferably at least 30%, and most preferably at least 35% at 20° C.

Most preferred are plant stanol fatty acid esters. Therefore, the plant sterol ester and/or plant stanol ester contains preferably plant stanol ester in an amount of at least 30%, more preferably at least 50%, still more preferably at least 70% and most preferably at least 90% by weight. Preferably the plant sterol ester and/or plant stanol ester has a solid fat content (SFC) of at least 20%, more preferably at least 25%, still more preferably at least 30%, and most preferably at least 35% at 20° C. and contains plant stanol ester in an amount of at least 30%, more preferably at least 50%, still more preferably at least 70% and most preferably at least 90% by weight.

Plant stanol fatty acid ester and the cholesterol lowering effects thereof, as well as a suitable method for its preparation, are disclosed in e.g. U.S. Pat. No. 6,174,560. Obviously plant sterol esters can also efficiently be produced by the production method disclosed in U.S. Pat. No. 6,174,560. Alternatively fatty acid esters of plant sterols and/or plant stanols can be produced by any suitable food grade method disclosed in the art. Commercially available plant sterol ester and/or plant stanol ester ingredients e.g. from Raisio Nutrition or BASF can be used.

The content of the plant sterol ester and/or plant stanol ester in the capsule filling can be analyzed by e.g. the method described by Lubinus et al. (Eur. J. Nutr. 2013, 52(3):997-1013) or by Esche et al. (J. Agric. Food Chem. 2012, 30; 60(21):5330-9).

The capsule filling of the present invention contains at least 1.0% by weight emulsifier. As used here the term "emulsifier" refers to a substance classified as an emulsifier in food legislation (Regulation (EC) No 1333/2008). The characterizing feature of the emulsifier is a structure in which one portion of the molecule is polar (hydrophilic) and the other non-polar (hydrophobic). HLB (hydrophilic lipophilic balance) scale is commonly used to generally describe the properties of emulsifiers. As used here, the emulsifier is a food grade substance, and its usage in food supplements is allowed by regulations (Regulation (EC) No 1333/2008). Preferably the emulsifier can be used based on the "quantum satis" principle in capsules, such as in softgel capsules.

It was found that capsule fillings having a high concentration of plant sterol ester and/or plant stanol ester, and still rapid disintegration in simulated gastric conditions, can be prepared by using emulsifiers in certain concentrations. Thus the capsule filling according to the invention contains at least 1.0%, preferably at least 2.0%, more preferably at least 4.0%, and most preferably at least 6.0% by weight emulsifier. Preferably the capsule filling contains at most 15%, more preferably at most 13%, still more preferably at most 10% and most preferably at most 8.0% by weight emulsifier.

One type of emulsifier or a mixture of at least two emulsifiers can be used. Typical examples of suitable emulsifiers include monoglycerides, such as distilled monoglycerides; diglycerides; monoglyceride esters such as acetic, lactic, succinic, citric or diacetyl tartaric acid esters of monoglycerides; lecithins; modified lecithins such as lysolecithins; polyglycerol esters; sorbitan esters; propylene glycol esters; sugar esters; and mixtures of any thereof. Preferred emulsifiers are those having a HLB value less than 12, more preferably at most 11 and most preferably at most 10. Preferably the emulsifier is selected from the group consisting of monoglycerides; diglycerides; lactic, citric or diacetyl tartaric acid esters of monoglycerides; lecithins; modified lecithins; polyglycerol esters and mixtures of any thereof. More preferably the emulsifier is selected from monoglycerides and/or diglycerides.

With monoglycerides surprisingly good results were obtained. Thus, the amount of monoglycerides is preferably at least 1.0%, more preferably at least 1.5%, still more preferably at least 2.0% and most preferably at least 2.5% by weight of the capsule filling. More preferably the emulsifier contains at least 30%, preferably at least 50%, more preferably at least 70% by weight monoglycerides and most preferably the emulsifier consists essentially of monoglycerides (i.e. at least 95% by weight). Even more preferably the emulsifier is a mixture of monoglycerides and diglycerides, wherein the amount of monoglycerides is at least 30%, preferably at least 50%, more preferably at least 70% and most preferably at least 95% by weight of the total amount of emulsifier.

Preferably the emulsifier contains at least 30%, preferably at least 50%, more preferably at least 70% and most preferably at least 95% monoglycerides having a melting temperature of at most 70° C., preferably at most 65° C., most preferably at most 60° C. and an iodine value of at least 30, more preferably at least 40, and most preferably at least 50. More preferably the melting temperature of the monoglycerides is at least 20° C., more preferably at least 25° C. and most preferably at least 30° C. By melting temperature is meant the temperature at which the monoglyceride is completely melted.

Especially suitable capsule fillings can be prepared by using a certain weight ratio of plant sterol ester and/or plant stanol ester to emulsifier. Preferably in the capsule filling the weight ratio of plant sterol ester and/or plant stanol ester to emulsifier is at least 6:1, more preferably at least 7:1, still more preferably at least 9:1 and most preferably at least 11:1. Preferably in the capsule filling the weight ratio of plant sterol ester and/or plant stanol ester to emulsifier is at most 50:1, more preferably at most 45:1, still more preferably at most 40:1, and most preferably at most 35:1.

In a preferred embodiment, the capsule filling comprises at least 87% by weight plant sterol ester and/or plant stanol ester and 2.0-13% by weight emulsifier. The weight ratio of plant sterol ester and/or plant stanol ester to emulsifier is preferably at least 7:1, more preferably at least 9:1 and most preferably at least 11:1. The weight ratio of plant sterol ester and/or plant stanol ester to emulsifier is preferably at most 45:1, more preferably at most 40:1 and most preferably at most 35:1. Preferred emulsifiers are those having a HLB value less than 12, more preferably at most 11 and most preferably at most 10. Preferably the emulsifier contains at least 30%, preferably at least 50%, more preferably at least 70% and most preferably at least 95% by weight monoglycerides having a melting temperature of at most 70° C., more preferably at most 65° C., most preferably at most 60° C. and an iodine value of at least 30, more preferably at least 40, and most preferably at least 50. Preferably the monoglycerides have a melting temperature of at least 20° C., more preferably at least 25° C. and most preferably at least 30° C. The amount of monoglycerides is preferably at least 1.0%, more preferably at least 1.5%, still more preferably at least 2.0% and most preferably at least 2.5% by weight of the capsule filling. Preferably the capsule filling of this embodiment is a softgel capsule filling.

In another preferred embodiment, the capsule filling comprises at least 90% by weight plant sterol ester and/or plant stanol ester and 2.0-10% by weight emulsifier. The weight ratio of plant sterol ester and/or plant stanol ester to emulsifier is preferably at least 9:1, and more preferably at least 11:1. The weight ratio of plant sterol ester and/or plant stanol ester to emulsifier is preferably at most 45:1, more preferably at most 40:1, and most preferably at most 35:1. Preferred emulsifiers are those having a HLB value less than 12, more preferably at most 11 and most preferably at most 10. Preferably the emulsifier contains at least 30%, preferably at least 50%, more preferably at least 70% and most preferably at least 95% by weight monoglycerides having a melting temperature of at most 70° C., more preferably at most 65° C., most preferably at most 60° C. and having an iodine value of at least 30, more preferably at least 40, and most preferably at least 50. Preferably the monoglycerides have a melting temperature of at least 20° C., more preferably at least 25° C. and most preferably at least 30° C. The amount of monoglycerides is preferably at least 1.0%, more preferably at least 1.5%, still more preferably at least 2.0% and most preferably at least 2.5% by weight of the capsule filling. Preferably the capsule filling of this embodiment is a softgel capsule filling.

The capsule filling according to the present invention may further contain free plant sterols and/or free plant stanols in an amount of 0-10%, preferably 0.1-10%, more preferably 0.1-5.0%, still more preferably 0.1-3.0% by weight. Even more preferably the amount of free plant sterol and/or free plant stanol is 0.1-2.0%, further more preferably 0.1-1.0% and most preferably 0.1-0.5% by weight of the filling. By "free plant sterols and/or free plant stanols" is meant that the plant sterols and/or plant stanols as defined above are in free form i.e. as an alcohol. This means that the hydroxyl group at carbon atom number 3 is free, not forming an ester or glycoside bond. Furthermore, it has been found that the free plant sterols and/or free plant stanols contained in many commercial plant sterol ester products and/or plant stanol ester products may during a prolonged storage (e.g. 6 months) of the gelatin capsule, form beneath the gelatin shell a hard free plant sterol and/or free plant stanol layer, which slows down the disintegration. The present invention preferably provides a capsule filling in which the amount of free plant sterols and/or free plant stanols is sufficiently low to avoid this problem. Restricting the amount of free plant sterols and/or free plant stanols contributes to a faster disintegration of the capsule filling, especially after prolonged storing of the capsules.

In a preferred embodiment, the capsule filling comprises at least 87% by weight plant sterol ester and/or plant stanol ester, 2.0-13% by weight emulsifier and 0.1-2.0% by weight free plant sterols and/or free plant stanols. Preferred emulsifiers are those having a HLB value less than 12, more preferably at most 11 and most preferably at most 10. The weight ratio of plant sterol ester and/or plant stanol ester to emulsifier is preferably at least 7:1, more preferably at least 9:1 and most preferably at least 11:1. The weight ratio of plant sterol ester and/or plant stanol ester to emulsifier is preferably at most 45:1, more preferably at most 40:1 and most preferably at most 35:1. Preferably the emulsifier contains at least 30%, preferably at least 50%, more preferably at least 70% and most preferably at least 95% by weight monoglycerides having a melting temperature of at most 70° C., more preferably at most 65° C., most preferably at most 60° C. and an iodine value of at least 30, more preferably at least 40, and most preferably at least 50. Preferably the monoglycerides have a melting temperature of at least 20° C., more preferably at least 25° C. and most preferably at least 30° C. The amount of monoglycerides is preferably at least 1.0%, more preferably at least 1.5%, still more preferably at least 2.0% and most preferably at least 2.5% by weight of the capsule filling. Preferably the capsule filling of this embodiment is a softgel capsule filling.

In another preferred embodiment, the capsule filling comprises at least 90% by weight plant sterol ester and/or plant stanol ester, 2.0-10% by weight emulsifier and 0.1-2.0% by weight free plant sterols and/or free plant stanols. Preferred emulsifiers are those having a HLB value less than 12, more preferably at most 11 and most preferably at most 10. The weight ratio of plant sterol ester and/or plant stanol ester to emulsifier is preferably at least 9:1, and more preferably at least 11:1. The weight ratio of plant sterol ester and/or plant stanol ester to emulsifier is preferably at most 45:1, more preferably at most 40:1, and most preferably at most 35:1. Preferably the emulsifier contains at least 30%, preferably at least 50%, more preferably at least 70% and most preferably at least 95% by weight monoglycerides having a melting temperature of at most 70° C., more preferably at most 65° C., most preferably at most 60° C. and an iodine value of at least 30, more preferably at least 40, and most preferably at least 50. Preferably the monoglycerides have a melting temperature of at least 20° C., more preferably at least 25° C. and most preferably at least 30° C. The amount of monoglycerides is preferably at least 1.0%, more preferably at least 1.5%, still more preferably at least 2.0% and most preferably at least 2.5% by weight of the capsule filling. Preferably the capsule filling of this embodiment is a softgel capsule filling.

The capsule filling of the present invention may further contain edible fat. By "edible fat" is here meant edible fats and oils that consist mainly (at least 90%, preferably at least 95% and most preferably at least 98% by weight) of triacylglycerols and that are suitable for human consumption. The edible fat can be commercially available vegetable oil and/or fat. It can be naturally occurring, i.e. un-modified but refined, bleached and deodorised, or modified, e.g. hydrogenated, fractionated, transesterified or contain structured triacylglycerols. Edible fat can also be a mixture of different edible fats. Preferably the edible fat is a vegetable oil or a blend of vegetable oils. Examples of suitable vegetable oils are canola/rapeseed oil, soybean oil, sunflower oil, olive oil, and corn oil.

It has been found that especially suitable capsule fillings can be prepared when the content of the edible fat is kept low or especially when essentially no edible fat is present in the filling. Preferably the capsule filling of the present invention may contain 0-8.0% by weight edible fat. More preferably the capsule filling contains 0.1-8.0%, still more preferably 0.1-4.0%, even more preferably 0.1-2.0% by weight edible fat. Most preferably the capsule filling of the present invention contains essentially no edible fat (i.e. 0 to less than 0.1% by weight edible fat). If the capsule filling contains edible fat, the weight ratio of plant sterol ester and/or plant stanol ester to the edible fat is preferably more than 10:1. More preferably the weight ratio of plant sterol ester and/or plant stanol ester to the edible fat is at least 11:1, still more preferably at least 12:1, even more preferably at least 13:1, further more preferably at least 22:1 and most preferably at least 23:1.

In a preferred embodiment, the capsule filling comprises at least 87% by weight plant sterol ester and/or plant stanol ester, 2.0-13% by weight emulsifier, 0.1-2.0% free plant sterols and/or free plant stanols and 0.1-4.0% by weight edible fat. The weight ratio of plant sterol ester and/or plant stanol ester to the emulsifier is preferably at least 7:1, more preferably at least 9:1 and most preferably at least 11:1. The weight ratio of plant sterol ester and/or plant stanol ester to emulsifier is preferably at most 50:1, more preferably at most 45:1 still more preferably at most 40:1 and most preferably at most 35:1. The weight ratio of plant sterol ester and/or plant stanol ester to the edible fat is at least 22:1. Preferred emulsifiers are those having a HLB value less than 12, more preferably at most 11 and most preferably at most 10. Preferably the emulsifier contains at least 30%, preferably at least 50%, more preferably at least 70% and most preferably at least 95% by weight monoglycerides having a melting temperature of at most 70° C., more preferably at most 65° C., most preferably at most 60° C. and an iodine value of at least 30, more preferably at least 40, and most preferably at least 50. Preferably the monoglycerides have a melting temperature of at least 20° C., more preferably at least 25° C. and most preferably at least 30° C. The amount of monoglycerides is preferably at least 1.0%, more preferably at least 1.5%, still more preferably at least 2.0% and most preferably at least 2.5% by weight of the capsule filling. The filling preferably has a solid fat content (SFC) of at least 20%, more preferably at least 25%, still more preferably at least 30%, and most preferably at least 35% at 20° C. Preferably the capsule filling of this embodiment is a softgel capsule filling.

In another preferred embodiment, the capsule filling comprises at least 87% by weight plant sterol ester and/or plant stanol ester, 2.0-13% by weight emulsifier, 0.1-2.0% free plant sterols and/or free plant stanols and 0 to less than 0.1% by weight edible fat (i.e. essentially no edible fat). The weight ratio of plant sterol ester and/or plant stanol ester to the emulsifier is preferably at least 7:1, more preferably at least 9:1 and most preferably at least 11:1. Preferred emulsifiers are those having a HLB value less than 12, more preferably at most 11 and most preferably at most 10. Preferably the emulsifier contains at least 30%, preferably at least 50%, more preferably at least 70% and most preferably at least 95% by weight monoglycerides having a melting temperature of at most 70° C., more preferably at most 65° C., most preferably at most 60° C. and an iodine value of at least 30, more preferably at least 40, and most preferably at least 50. Preferably the monoglycerides have a melting temperature of at least 20° C., more preferably at least 25° C. and most preferably at least 30° C. The amount of monoglycerides is preferably at least 1.0%, more preferably at least 1.5%, still more preferably at least 2.0% and most preferably at least 2.5% by weight of the capsule filling. The filling preferably has a solid fat content (SFC) of at least 20%, more preferably at least 25%, still more preferably at least 30%, and most preferably at least 35% at 20° C. Preferably the capsule filling of this embodiment is a softgel capsule filling.

The capsule filling of the invention may also contain other ingredients, especially fat-soluble ingredients with beneficial health effects, such as fat soluble vitamins (e.g. vitamin D), tocopherols, tocotrienols, coenzyme Q10, vitamin K, antioxidants and mixtures of any thereof.

Preferably the capsule filling of the present invention does not contain water (i.e. it may contain at most 0.1% by weight water). The capsule filling is preferably free of excipients. These are often used in pharmaceutical capsules and tablets. Examples of such excipients include silicon dioxide, microcrystalline cellulose, starch, maltodextrin and sugars. The emulsifier, the optional edible fat, as well as the optional free plant sterols and/or free plant stanols, all defined in the present invention, are obviously hereby excluded from the term excipient.

Another object of the present invention is to provide a method of preparing the capsule according to the present invention. The method comprises at least the following steps:
a) melting plant sterol ester and/or plant stanol ester, preferably at a temperature of at least 40° C., more preferably at 40-80° C., to obtain a clear solution, and keeping the melted plant sterol ester and/or plant stanol ester at this temperature for at least 10 minutes,
b) melting emulsifier, unless already liquid at room temperature, preferably at a temperature of at least 40° C., more preferably at 40-80° C. to obtain a clear solution,
c) mixing plant sterol ester and/or plant stanol ester and emulsifier,
d) stirring and keeping the obtained mixture at a temperature of at least 40° C. for at least 10 minutes,
e) dosing the melted mixture, preferably at a temperature of at least 10° C. higher than the temperature at which the mixture becomes clear, to a capsule manufacturing line,
f) using the melted mixture to fill a capsule, preferably a softgel capsule.

In the method plant sterol ester and/or plant stanol ester is heated until it is totally melted and a clear solution is obtained. If free plant sterols and/or free plant stanols are used, they can be suspended into the plant sterol ester and/or plant stanol ester. Often the commercial plant sterol ester and/or plant stanol ester ingredient contains both plant sterol ester and/or plant stanol ester and free plant sterols and/or free plant stanols. The melt is still kept at 40-80° C. for at least about 10 minutes to destroy the so called crystal memory of the plant sterol ester and/or plant stanol ester. Also the emulsifier is melted, if it is not liquid at room temperature. If edible fat is used, it is also melted, if not liquid at room temperature. All ingredients (including optional other ingredients) are then mixed. It is also possible to first mix the plant sterol ester and/or plant stanol ester with the emulsifier and then perform the melting step of the mixture. It is further possible to first melt the plant sterol ester and/or plant stanol ester, then add the emulsifier and continue the melting process until the mixture is totally melted. Thus, step c) may be performed before step a), before step b), but most preferably after step b). Important is however that the plant sterol ester and/or plant stanol ester is in melted form long enough to destroy its crystal memory. After mixing all the ingredients together the mixture is still kept in melted form with gentle stirring for at least about 10 minutes to ensure the mixture is homogenous. The mixture is then dosed into a capsule manufacturing line preferably at a temperature of about at least 10° C. above the temperature at which this mixture becomes clear (i.e. totally melted). Finally, capsules are formed by producing a shell around the dosed mixture at the encapsulation line.

Because the capsule filling of the invention has a high plant sterol ester and/or plant stanol ester content, the daily effective dose of plant sterol ester and/or plant stanol ester can be incorporated in a few capsules. The preferred daily dose of plant sterol ester and/or plant stanol ester is at least 0.8 g, more preferably at least 1.3 g, still more preferably at least 1.7 g, even more preferably at least 2.5 g and most preferably the daily dose of plant sterol ester and/or plant stanol ester is at least 3.4 g. The preferred daily dose of plant sterol ester and/or plant stanol ester is at most 10 g, more preferably at most 8 g, still more preferably at most 7 g, even more preferably at most 6 g, and most preferably at most 5 g.

The daily dose of plant sterol ester and/or plant stanol ester is preferably provided by 0.8-13 g of the capsule filling, i.e. the daily dose of the capsule filling is preferably 0.8-13 g. More preferably the daily dose of plant sterol ester and/or plant stanol ester is provided by 1.4-10 g, still more preferably 1.8-9 g, even more preferably 2.6-8 g, and most preferably 3.6-6 g of the softgel capsule filling. Preferably the daily dose of plant sterol ester and/or plant stanol ester is provided by 1-15 capsules, i.e. the recommended daily number of the capsules is 1-15. More preferably the daily dose of plant sterol ester and/or plant stanol ester is provided by 1-12, still more preferably by 1-10, even more preferably by 1-7, and most preferably by 1-4 capsules. Softgel capsules can have any shape. The most commons softgel capsule shapes are e.g. round, oval and oblong, but also special shapes, such as animal shapes, can be produced.

A preferred embodiment of the present invention is a capsule comprising a shell and a filling that comprises plant sterol ester and/or plant stanol ester in an amount of 87-99% by weight, an emulsifier in an amount of 1.0-13% by weight, free plant sterols and/or free plant stanols in an amount of 0.1-2.0% by weight and edible fat in an amount of 0.1-8.0% by weight of the capsule filling. In this embodiment, the capsule is preferably a softgel capsule. Preferably the capsule filling has a solid fat content (SFC) of at least 20%, more preferably at least 25%, still more preferably at least 30%, and most preferably at least 35% at 20° C. Preferably in this embodiment, plant sterol ester and/or plant stanol ester contains plant stanol ester in an amount of at least 30%, more preferably at least 50%, still more preferably at least 70% and most preferably at least 90% by weight of the plant sterol ester and/or plant stanol ester. Preferably the plant sterol ester and/or plant stanol ester has a solid fat content (SFC) of at least 20%, more preferably at least 25%, still more preferably at least 30%, and most preferably at least 35% at 20° C. In this embodiment, the weight ratio of plant sterol ester and/or plant stanol ester to the emulsifier is preferably at least 7:1, more preferably at least 9:1 and most preferably at least 11:1. Preferred emulsifiers are those having a HLB value less than 12, more preferably at most 11 and most preferably at most 10. More preferably the emulsifier contains at least 30%, preferably at least 50%, more preferably at least 70% and most preferably at least 95% by weight monoglycerides having a melting temperature of at most 70° C., preferably at most 65° C., most preferably at most 60° C. and an iodine value of at least 30, more preferably at least 40, and most preferably at least 50. Preferably the monoglycerides have a melting temperature of at least 20° C., more preferably at least 25° C. and most preferably at least 30° C. The amount of monoglycerides is preferably at least 1.0%, more preferably at least 1.5%, still more preferably at least 2.0% and most preferably at least 2.5% by weight of the capsule filling. If edible fat is present in the capsule filling of this embodiment, the weight ratio of the plant sterol ester and/or plant stanol ester to the edible fat is preferably more than 11:1.

A preferred embodiment of the present invention is a capsule comprising a shell and a filling that comprises plant sterol ester and/or plant stanol ester in an amount of 87-98% by weight, an emulsifier in an amount of 2.0-13% by weight, free plant sterols and/or free plant stanols in an amount of 0.1-2.0% by weight and edible fat in an amount of 0.1-4.0% by weight of the capsule filling. In this embodiment, the capsule is preferably a softgel capsule. Preferably the capsule filling has a solid fat content (SFC) of at least 20%, more preferably at least 25%, still more preferably at least 30%, and most preferably at least 35% at 20° C. Preferably in this embodiment, plant sterol ester and/or plant stanol ester contains plant stanol ester in an amount of at least 30%, more preferably at least 50%, still more preferably at least 70% and most preferably at least 90% by weight of the plant sterol ester and/or plant stanol ester. Preferably the plant sterol ester and/or plant stanol ester has a solid fat content (SFC) of at least 20%, more preferably at least 25%, still more preferably at least 30%, and most preferably at least 35% at 20° C. In this embodiment, the weight ratio of plant sterol ester and/or plant stanol ester to the emulsifier is preferably at least 7:1, more preferably at least 9:1 and most preferably at least 11:1. In this embodiment, the weight ratio of plant sterol ester and/or plant stanol ester to the emulsifier is preferably at most 50:1, more preferably at most 45:1, even more preferably at most 40:1 and most preferably at most 35:1. Preferred emulsifiers are those having a HLB value less than 12, more preferably at most 11 and most preferably at most 10. More preferably the emulsifier contains at least 30%, preferably at least 50%, more preferably at least 70% and most preferably at least 95% by weight monoglycerides having a melting temperature of at most 70° C., preferably at most 65° C., most preferably at most 60° C. and an iodine value of at least 30, more preferably at least 40, and most preferably at least 50. Preferably the monoglycerides have a melting temperature of at least 20° C., more preferably at least 25° C. and most preferably at least 30° C. The amount of monoglycerides is preferably at least 1.0%, more preferably at least 1.5%, still more preferably at least 2.0% and most preferably at least 2.5% by weight of the capsule filling. If edible fat is present in the capsule filling of this embodiment, the weight ratio of the plant sterol ester and/or plant stanol ester to the edible fat is preferably at least 22:1.

Another preferred embodiment of the present invention is a capsule comprising a shell and a filling that comprises plant sterol ester and/or plant stanol ester in an amount of 87-98% by weight, an emulsifier in an amount of 2.0-13% by weight, free plant sterols and/or free plant stanols in an amount of 0.1-2.0% by weight and edible fat in an amount of 0.1-4.0% by weight of the capsule filling. In this embodiment, the capsule is preferably a softgel capsule. Preferably the capsule filling has a solid fat content (SFC) of at least 20%, more preferably at least 25%, still more preferably at least 30%, and most preferably at least 35% at 20° C. Preferably in this embodiment, plant sterol ester and/or plant stanol ester contains plant stanol ester in an amount of at least 30%, more preferably at least 50%, still more preferably at least 70% and most preferably at least 90% by weight of the plant sterol ester and/or plant stanol ester. Preferably the plant sterol ester and/or plant stanol ester has a solid fat content (SFC) of at least 20%, more preferably at least 25%, still more preferably at least 30%, and most preferably at least 35% at 20° C. In this embodiment, the weight ratio of plant sterol ester and/or plant stanol ester to the emulsifier is preferably at least 7:1, more preferably at least 9:1 and most preferably at least 11:1. In this embodiment, the weight ratio of plant sterol ester and/or plant stanol ester to the emulsifier is preferably at most 50:1, more preferably at most 45:1, still more preferably at most 40:1 and most preferably at most 35:1. In this embodiment, the emulsifier preferably has a HLB value of less than 12, more preferably at most 11 and most preferably at most 10. Preferably the emulsifier is selected from monoglycerides; diglycerides; lactic, citric or diacetyl tartaric acid esters of monoglycerides; lecithins; modified lecithins; polyglycerol esters and mixtures of any thereof. More preferably the emulsifier contains, and still more preferably it consists of monoglycerides and/or diglycerides. If edible fat is present in the capsule filling of this embodiment, the weight ratio of the plant sterol ester and/or plant stanol ester to the edible fat is preferably at least 22:1.

A further object of the present invention is the before mentioned capsule for use as a medicament, especially for lowering serum LDL cholesterol. By medicament is here meant a substance that is physiologically active in preventing or alleviating a disease or a risk factor of a disease. The invention is further directed to a method for lowering serum LDL cholesterol in a subject in need thereof, wherein the capsule according to the invention is administered to the subject. Thereby the subject ingests capsules according to the invention in such an amount that an effective amount of plant sterol ester and/or plant stanol ester is ingested, as disclosed in this description.

In this description the amounts given in percentages mean percentage by weight (wt-%) of the capsule filling unless otherwise stated. Both comprising and containing mean "containing at least" in this context. Consisting of is a closed definition and means is.

The invention will be described in greater detail by means of the following non-limiting examples.

Example 1 Comparative

Two reference capsule fillings (R1-R2) were prepared. The capsule fillings contained either plant stanol ester as such (R1) or mixed with vegetable oil (R2). The disintegration of these fillings was tested in simulated gastric fluid.

Commercial plant stanol ester ingredient Benecol Classic was used. It contained 0.4% free stanols and 99.6% plant stanol ester. Plant stanol ester was esterified with rapeseed oil fatty acids. The plant stanol ester ingredient was melted at 60° C. and kept at this temperature for 15 minutes after complete melting. In the case of R1 the melted plant stanol ester ingredient was dosed as such into moulds that provided a solidified filling of 1 g. In the case of R2, rapeseed oil was mixed with the melted plant stanol ester ingredient. This mixture was then dosed into moulds of the size that provided a solidified filling of 1 g. Both R1 and R2 were allowed to cool and solidify for 70 hours at room temperature (22° C.).

| INGREDIENTS | R1, comparative | R2, comparative |
|---|---|---|
| | % of the filling | |
| Plant stanol ester ingredient (Benecol Classic)* | 100 | 90 |
| Rapeseed oil | — | 10 |

*containing 99.6% by weight plant stanol ester, i.e. plant stanol ester concentration in recipe R1 is 99.6% and in R2 89.6% by weight Simulated gastric fluid, pH 1.2, was prepared according to the instructions of United States Pharmacopeia for Simulated Gastric Fluid TS. Sodium chloride (2 g) was dissolved in hydrochloric acid (7 ml) and water (987.8 ml). The fluid was tempered at 38° C. in a shaking water bath and pepsin (3.2 g purified pepsin 2000 FIR-U/g, EC 3.4.23.1 Merck) was added. The fluid was let to clarify for two minutes in the water bath. 300 ml of the fluid was transferred to a tempered bottle. 1 g of the filling (R1 or R2) was expelled from the mould and added into the simulated gastric fluid in the bottle and the bottle was placed in a shaking water bath (38° C., shaking 155 oscillations per minute). The disintegration of the filling was visually continuously observed for a period of 20 minutes.

| | R1 comparative | R2 comparative |
|---|---|---|
| DISINTEGRATION TEST (time in minutes) | | |
| Stage 1: The filling is as one particle and there is no change in its appearance | From 0 min to the timef o Stage 2 | From 0 min to the time of Stage 2 |
| Stage 2: Appearance of the filling has turned transparent, but the filling is still as one particle | 6 min | 7 min |

-continued

| | R1 comparative | R2 comparative |
|---|---|---|
| Stage 3: Several (>2) disintegrated particles in the fluid | remained as one particle | remained as one particle |
| Stage 4: The fluid is cloudy | no | no | no = this stage was not reached during the follow-up time

None of the reference capsule fillings was disintegrated during the 20 min follow-up period in the simulated human gastric fluid test. After the 20 min continuous follow-up period, the fillings were left in the simulated human gastric fluid at 38° C. and observed every half hour until 3 hours had passed from the beginning of the test. The fillings did not disintegrate (reach stage 3 or 4 in the disintegration test) even during this 3 hour period. Thus the disintegration of these fillings, representing the prior known plant sterol ester and/or plant stanol ester capsule fillings, was very slow and inefficient in the simulated gastric fluid. This slow disintegration in the simulated gastric fluid test indicates that these fillings are not effectively disintegrated in the stomach. This may partly explain the poor or lower than expected serum LDL cholesterol lowering results obtained in published clinical trials with plant sterol ester and/or plant stanol ester softgel capsules.

Example 2

Capsule fillings (T1-T3) containing plant stanol ester and emulsifier were prepared and tested. The plant stanol ester concentration was high (89.6%), and comparable to the concentration of the filling R2 in the Example 1.

Plant stanol ester ingredient and an emulsifier were melted at 60° C. and mixed together. The emulsifiers were monoglycerides (distilled monoglycerides, melting temperature 45° C., iodine value 105), lactic acid esters of mono-diglycerides (melting temperature 45° C.), lecithin (sunflower lecithin, fluid at room temperature) and PGE (tetraglycerol ester, melting temperature at 40° C.). The ratio of the plant stanol ester to the emulsifier was 9:1.

The obtained mixtures were dosed into moulds of the size that provided solidified filling of 1 g. Each mixture was dosed into duplicate moulds. The mixtures were allowed to cool and solidify at room temperature (22° C.) for 70 hours. Then one of the duplicate moulds was emptied and the disintegration of the filling was tested as described in Example 1, with a 20 minutes follow-up period. The other duplicate mould was stored at room temperature for 6 months, after which the disintegration test was done.

|  | T1 | T2 | T3 | T4 |
|---|---|---|---|---|
| INGREDIENTS | % of the filling | | | |
| Plant stanol ester ingredient (Benecol Classic)* | 90 | 90 | 90 | 90 |
| Monoglyceride (Palsgaard DMG 0295) | 10 | | | |
| Lactic acid esters of mono-diglycerides (Grinsted Lactem) | | 10 | | |
| Lecithin (Solec SF-10) | | | 10 | |
| PGE (Grinsted PGE 20) | | | | 10 |
| Plant stanol ester to emulsifier - ratio | 9:1 | 9:1 | 9:1 | 9:1 |
| DISINTEGRATION TEST (time in minutes) | | | | |
| Stage 1: The filling is as one particle and there is no change in its appearance | From 0 min to the time of Stage 2 | From 0 min to the time of Stage 2 | From 0 min to the time of Stage 2 | From 0 min to the time of Stage 2 |
| Stage 2: Appearance of the filling has turned (partly or totally) transparent, but is still as one particle | 2 min | 2 min | 4 min | 2 min |
| Stage 3: Several (>2) disintegrated particles in the fluid | 4 min | 11 min | 7 min** | 15 min |
| Stage 4: The fluid is cloudy | 11 min | no | 20 min | 15 min |

*containing 99.6% by weight plant stanol ester and 0.4% by weight free plant stanols, i.e. plant stanol ester concentration in the recipes is 89.6% by weight
no = this stage was not reached during the follow-up time
**disintegrated only into two particles All the test capsule fillings (T1-T4) were disintegrated in the simulated gastric fluid, pH 1.2, in 20 minutes. Filling T1 (containing 10% monoglyceride) disintegrated into several particles that could be visually distinguished already in 4 minutes. The simulated gastric fluid turned cloudy in 11 minutes, indicating that the filling was disintegrated into fine particles that were distributed throughout the fluid. The filling T2 disintegrated somewhat differently yielding several visually distinguishable small particles in 11 minutes, but no cloudy fluid in the follow-up period of 20 minutes. T3 disintegrated only into two big particles in 7 minutes. However, because the simulated gastric fluid turned cloudy in 20 minutes, also some smaller particles must have diverged during the 20 minute follow-up period. T4 disintegrated into several particles and the simulated gastric fluid turned cloudy simultaneously at 15 minutes.

Surprisingly the disintegration of all the test fillings (T1-T4) was faster than the disintegration of the corresponding reference filling R2 in Example 1. Plant stanol ester and also all the emulsifiers, except lecithin (recipe T3), have melting temperature of 40° C. or higher unlike rapeseed oil used in recipe R2 in Example 1. All the fillings (T1-T4) were solid at room temperature before the disintegration test. Still all the fillings were rapidly disintegrated into several particles and/or formed cloudy fluids. The most efficient (time to achieve stages 3 and/or 4 in the test) disintegration was achieved with the filling T1, which contained monoglycerides as the emulsifier.

After 6 months, the fillings T1-T4 were expelled from the duplicate moulds that had been stored at room temperature, and the simulated gastric fluid test was done in a similar way as described above. The results did not differ from the results obtained with the fillings T1-T4 that had been tested after 70 hours solidification.

Example 3

Capsule fillings containing plant stanol ester (89.6%), emulsifier and edible fat were tested. Plant stanol ester ingredient and emulsifier (monoglycerides) were melted at 60° C. and mixed together. Rapeseed oil was mixed into this mixture at 60° C. The mixture was dosed into moulds and allowed to cool and solidify at room temperature (22° C.) for 70 hours. Disintegration of the fillings was tested as described in Example 1 with a 20 minutes follow-up period.

|  | T4 | T5 | T6 |
|---|---|---|---|
| INGREDIENTS | % of the filling | | |
| Plant stanol ester ingredient (Benecol Classic)* | 90 | 90 | 90 |
| Rapeseed oil | 8.0 | 4.0 | 2.0 |
| Monoglyceride (Palsgaard DMG 0295) | 2.0 | 6.0 | 8.0 |
| Plant stanol ester to emulsifier - ratio | 45:1 | 15:1 | 11:1 |
| Plant stanol ester to edible fat - ratio | 11:1 | 22:1 | 45:1 |
| DISINTEGRATION TEST (time in minutes) | | | |
| Stage 1: The filling is as one particle and there is no change in its appearance | From 0 min to the time of Stage 2 | From 0 min to the time of Stage 2 | From 0 min to the time of Stage 2 |

|  | T4 | T5 | T6 |
|---|---|---|---|
| Stage 2: Appearance of the filling has turned (partly or totally) transparent, but the filling is still as one particle | 2 min | 2 min | 1 min |
| Stage 3: Several (>2) disintegrated particles in the fluid | 15 min | 4 min | 4 min |
| Stage 4: The fluid is cloudy | 10 min** | 16 min | 6 min |

*containing 99.6% by weight plant stanol ester and 0.4% by weight free plant stanols, i.e. plant stanol ester concentration in the recipes is 89.6% by weight
**the fillings was still as one big particle at 10 min, but the fluid started to turn cloudy Fillings T5 and T6 containing 90% plant stanol ester, 6-8% monoglyceride and 2-4% vegetable oil disintegrated into several particles very rapidly (4 minutes), comparably to the filling T1 in Example 2. Filling T4 containing 8% rapeseed oil and 2% monoglyceride disintegrated somewhat differently yielding several visually distinguishable small particles only in 15 minutes. However, smaller particles must have diverged already earlier from the filling, as a cloudy fluid was observed already in 10 minutes.

Example 4

Filling containing plant stanol ester (89.6%), vegetable oil (8%) and a different kind of monoglyceride (2%) as an emulsifier.

In addition to the monoglyceride used in the previous examples, another monoglyceride was tested in the capsule filling. The monoglycerides were Dimodan BP-PEL/B (distilled monoglyceride, dropping point 60° C., iodine value 40). The filling was prepared in a similar way as described in Example 3, and the disintegration test was done as described in Example 1 with a 20 minutes follow-up period.

|  | T7 |
|---|---|
| INGREDIENTS | % of the filling |
| Plant stanol ester ingredient (Benecol Classic)* | 90 |
| Rapeseed oil | 8 |
| Monoglyceride (Dimodan BP-PEL/B) | 2 |

|  | T7 |
|---|---|
| Plant stanol ester to emulsifier - ratio | 45:1 |
| Plant stanol ester to edible fat - ratio | 11:1 |
| DISINTEGRATION TEST (time in minutes) | |
| Stage 1: The filling is as one particle and there is no change in its appearance | From 0 min to the time of Stage 2 |
| Stage 2: Appearance of the filling has turned (partly or totally) transparent, but the filling is still as one particle | 2 min |
| Stage 3: Several (>2) disintegrated particles in the fluid | 10 min** |
| Stage 4: The fluid is cloudy | 10 min |

*containing 99.6% by weight plant stanol ester and 0.4% by weight free plant stanols, i.e. plant stanol ester concentration in the recipe is 89.6% by weight
**disintegrated only into two particles Filling T7 contained 2% monoglycerides and 8% rapeseed oil. It disintegrated into two visually distinguishable big particles during the 20 minutes follow-up, but formed a cloudy fluid already in 10 minutes, indicating that smaller particles had diverged from the filling.

Example 5

Fillings containing higher plant stanol ester concentration (91.6% and 94.6%), monoglycerides and optionally also vegetable oil (T10). The fillings were prepared in a similar way as described in Example 3, and the disintegration test was done as described in Example 1 with a 20 minutes follow-up period.

|  | T8 | T9 | T10 |
|---|---|---|---|
| INGREDIENTS | % of the filling | | |
| Plant stanol ester ingredient (Benecol Classic)* | 92 | 95 | 92 |
| Rapeseed oil |  |  | 3.0 |
| Monoglyceride (Palsgaard DMG 0295) | 8.0 | 5.0 | 5.0 |
| Plant stanol ester to emulsifier - ratio | 11:1 | 19:1 | 18:1 |
| Plant stanol ester to edible fat - ratio | — | — | 31:1 |
| DISINTEGRATION TEST (time in minutes) | | | |
| Time (minutes, seconds) | | | |
| Stage 1: The filling is as one particle and there is no change in its appearance | From 0 min to the the time of Stage 2 | From 0 min to the time of Stage 2 | From 0 min to the time of Stage 2 |
| Stage 2: Appearance of the filling has turned (partly or totally) transparent, but the filling is still as one particle | 3 min | 3 min | 2 min |
| Stage 3: Several (>2) disintegrated particles in the fluid | 4 min | 3 min | 4 min |
| Stage 4: The fluid is cloudy | 6 min | 6 min | 14 min |

*containing 99.6% by weight plant stanol ester and 0.4% by weight free plant stanols Although the fillings T8-T10 contained 92% (T8, T10) or 95% (T9) plant stanol ester, they were rapidly disintegrated into several particles and/or formed a cloudy fluid.

The invention claimed is:

1. A therapeutic capsule comprising a shell and a filling, wherein the filling consists of:
   serum LDL cholesterol lowering plant sterol ester and/or plant stanol ester in an amount of at least 85% by weight;
   emulsifier selected from the group consisting of monoglycerides; diglycerides; monoglyceride esters; lecithins; modified lecithins; polyglycerol esters; sorbitan esters; propylene glycol esters; sugar esters; and mixtures of any thereof in an amount of at least 1.0% by weight;
   free plant sterols and/or free plant stanols in an amount of 0-10% by weight;
   edible fat in an amount of 0-8.0% by weight; and
   water in an amount of 0-0.1% by weight.

2. The capsule according to claim 1, wherein the amount of plant sterol ester and/or plant stanol ester is at least 87% by weight of the filling.

3. The capsule according to claim 1, wherein the amount of plant sterol ester and/or plant stanol ester is at most 99% by weight of the filling.

4. The capsule according to claim 1, wherein the amount of emulsifier is at least 2.0% by weight of the filling.

5. The capsule according to claim 1, wherein the amount of emulsifier is at most 15% by weight of the filling.

6. The capsule according to claim 1, wherein the emulsifier is food grade.

7. The capsule according to claim 1, wherein the weight ratio of plant sterol ester and/or plant stanol ester to emulsifier is at most 50:1.

8. The capsule according to claim 1, wherein the weight ratio of plant sterol ester and/or plant stanol ester to emulsifier is at least 6:1.

9. The capsule according to claim 1, wherein the monoglyceride ester is selected from acetic, lactic, succinic, citric or diacetyl tartaric acid esters and mixtures of any thereof.

10. The capsule according to claim 1, wherein the emulsifier has a HLB value of less than 12.

11. The capsule according to claim 1, wherein the emulsifier comprises monoglycerides in an amount of at least 30% by weight.

12. The capsule according to claim 1, wherein the filling comprises monoglycerides in an amount of at least 1.0% by weight.

13. The capsule according to claim 1, wherein the monoglycerides have a melting temperature of at most 70° C.

14. The capsule according to claim 1, wherein the monoglycerides have a melting temperature of at least 20° C.

15. The capsule according to claim 1, wherein the monoglycerides have an iodine value of at least 30.

16. The capsule according to claim 1, wherein the filling comprises free plant sterols and/or free plant stanols in an amount of 0.1-10% by weight.

17. The capsule according to claim 1, wherein the filling comprises edible fat in an amount of 0.1-8.0% by weight.

18. The capsule according to claim 1, wherein the filling comprises essentially no edible fat.

19. The capsule according to claim 17, wherein the edible fat is vegetable oil.

20. The capsule according to claim 17, wherein the weight ratio of plant sterol ester and/or plant stanol ester to edible fat is more than 22:1.

21. The capsule according to claim 1, wherein the capsule is a softgel capsule.

22. The capsule according to claim 1, wherein the plant sterol ester and/or plant stanol ester comprises plant stanol ester in an amount of at least 30% by weight.

23. The capsule according to claim 1, wherein plant sterol ester and/or plant stanol ester has a solid fat content (SFC) of at least 20% at 20° C.

24. The capsule according to claim 1, wherein the filling has a solid fat content (SFC) of at least 20% at 20° C.

25. The capsule according to claim 1, wherein the filling disintegrates at 38° C. in simulated gastric fluid within 20 minute.

26. The capsule according to claim 1, wherein the emulsifier is a monoglyceride, a diglyceride or both.

27. The capsule according to claim 1, wherein water is present in an amount of between 0.0 to 0.1% by weight.

28. A therapeutic capsule comprising a shell and a filling, wherein the filling consists of:
   serum LDL cholesterol lowering plant sterol ester and/or plant stanol ester in an amount of at least 85% by weight;
   emulsifier selected from the group consisting of monoglycerides; diglycerides; monoglyceride esters; lecithins; modified lecithins; polyglycerol esters; sorbitan esters; propylene glycol esters; sugar esters; and mixtures of any thereof in an amount of at least 1.0% by weight;
   free plant sterols and/or free plant stanols in an amount of 0-10% by weight;
   edible fat in an amount of 0-8.0% by weight; water in an amount of 0-0.1% by weight; and
   an ingredient selected from the group consisting of fat soluble vitamins, tocopherols, tocotrienols, coenzyme Q10, vitamin K, antioxidants and any combinations thereof.

29. A therapeutic capsule comprising a shell and a filling, wherein the filling consists of:
   serum LDL cholesterol lowering plant sterol ester and/or plant stanol ester in an amount of 85-99% by weight;
   emulsifier selected from the group consisting of monoglycerides; diglycerides; monoglyceride esters; lecithins; modified lecithins; polyglycerol esters; sorbitan esters; propylene glycol esters; sugar esters; and mixtures of any thereof in an amount of at least 1.0% by weight;
   free plant sterols and/or free plant stanols in an amount of 0-10% by weight;
   edible fat in an amount of 0-8.0% by weight; water in an amount of 0-0.1% by weight; and an antioxidant.

* * * * *